United States Patent [19]

Dahle et al.

[11] 4,030,346

[45] June 21, 1977

[54] MAGNETOELASTIC TRANSDUCER ARRANGEMENT

[75] Inventors: Orvar Dahle; Folke von Knorring; Sture Siby, all of Vasteras, Sweden

[73] Assignee: ASEA Aktiebolag, Vasteras, Sweden

[22] Filed: Oct. 6, 1975

[21] Appl. No.: 619,803

[30] Foreign Application Priority Data

Oct. 25, 1974 Sweden .............................. 7413444

[52] U.S. Cl. .......................... 73/88.5 R; 73/DIG. 2; 324/34 ST
[51] Int. Cl.² ........................................... G01B 7/24
[58] Field of Search .................. 73/88.5 R, DIG. 2; 324/34 ST, 34 MA; 336/20

[56] References Cited

UNITED STATES PATENTS

| 2,912,642 | 11/1959 | Dahle | 73/DIG. 2 |
| 3,798,537 | 3/1974 | Dahm | 324/34 ST |
| 3,861,206 | 1/1975 | Kawafune et al. | 73/DIG. 2 |

Primary Examiner—Charles A. Ruehl
Attorney, Agent, or Firm—Watson, Cole, Grindle & Watson

[57] ABSTRACT

A transducer including four pins arranged at the corners of a square and provided with exciting and sensing windings are fixed either to the surface of a body of magnetic material to measure stresses therein or to a plate of magnetic material fixed to the body where the body is of non-magnetic material or has undesirable magnetic characteristics.

4 Claims, 6 Drawing Figures

U.S. Patent      June 21, 1977      4,030,346
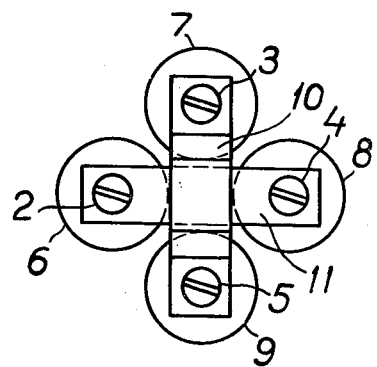
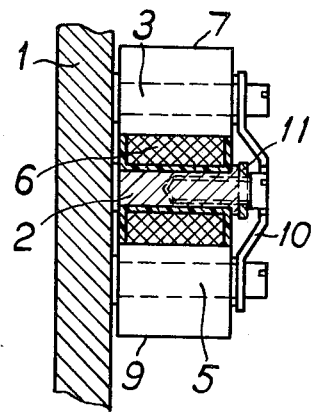
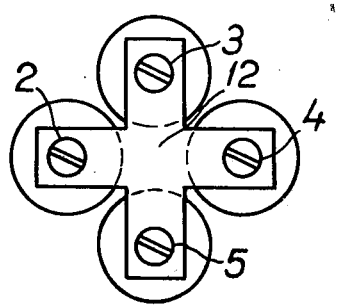
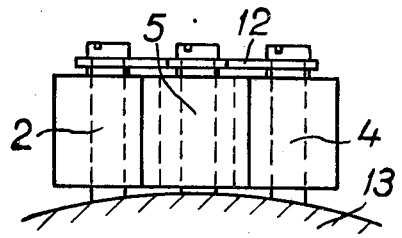
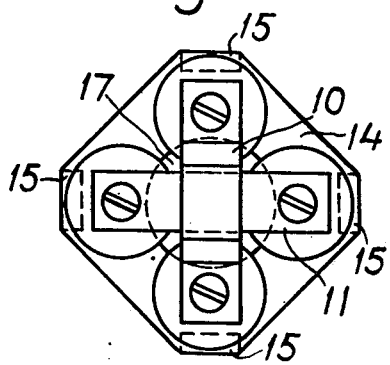
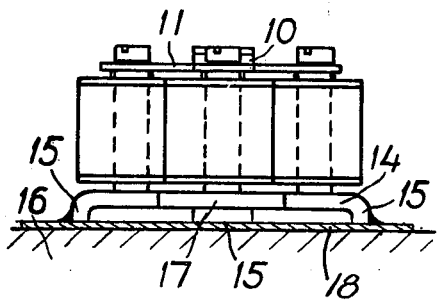

MAGNETOELASTIC TRANSDUCER ARRANGEMENT

BACKGROUND OF THE INVENTION

1. Field of the Invention

The invention relates to a transducer arrangement for measuring stresses in bodies.

2. The Prior Art

In U.S. Pat. No. 2,912,642 there is disclosed and described a transducer to be used when measuring mechanical stresses in objects of magnetic material. The transducer has a magnetizing part for generating a magnetic flux in the measuring object, and a measuring part for sensing the changes of the magnetic field configuration in the object which occur when it is subjected to the effect of mechanical forces. During measuring, the transducer is placed so that the air gaps between the transducer and the object are as small as possible and are kept constant to the utmost possible extent.

SUMMARY OF THE INVENTION

The present invention provides a solution to the problem of applying a transducer of the type in question on an object, and relates to a method for manufacturing a magnetoelastic transducer to be used for measuring mechanical stresses in a body of magnetic material. The body may be constituted by the object itself or by another body, for example in the form of a plate of magnetic material, which is attached to the measuring object.

More particularly, the transducer includes four pins of magnetic material arranged at the corners of a square and provided with exciting and sensing windings and with magnetic yokes connecting diagonally opposite pins which pins are welded either to the surface of a body of magnetic material to measure stresses therein or to a plate of magnetic material welded to the body where the body is of non-magnetic material or has undesirable magnetic characteristics By welding the pins on to the body, a very solid attachment of the transducer is obtained. Furthermore, the possibilities of measurement errors, which in previous constructions could be caused by changes in the size of the air gaps, are eliminated.

BRIEF DESCRIPTION OF THE DRAWINGS

The invention will be described with the help of the accompanying drawing, in which FIGS. 1a and 1b, are a top view and a side view, respectively, partly in section of a transducer with separate yokes, which transducer is applied directly on a plane measuring object.

FIG. 2a shows the use of a cross-formed yoke and

FIG. 2b shows the transducer applied on a curved surface.

FIGS. 3a and 3b, respectively, show a transducer arranged on a plate serving as a body, which plate is fastened to the measuring object.

DESCRIPTION OF THE PREFERRED EMBODIMENTS

FIGS. 1a and 1b show a transducer applied on a body 1 of magnetic material and which in this case is assumed to be part of the object which is exposed to mechanical forces. Four pins 2, 3, 4 and 5 are fastened by means of stud welding, so that the pins are firmly attached to the body without air gaps. Around each pin there is placed a winding 6, 7, 8 and 9. The free ends of the pins 2 and 4 and 3 and 5, respectively, are joined to each other by yokes 10 and 11, respectively, of magnetic material. In this way a first magnetic circuit is formed consisting of the pins 2 and 4, the windings 6 and 8, the yoke 11 and the body 1. A second magnetic circuit is formed of the pins 3 and 5, the windings 7 and 9, the yoke 10 and the body 1. At least one of the windings of one of these circuits is connected to an excitation voltage source (not shown) for generating a magnetic field in the body. The coils of the second circuit are connected to a measuring device for indicating the changes in the field configuration which occur in the body when the object is subjected to mechanical forces.

FIG. 2a shows a top view of a transducer where all four pins have their free ends connected to a common cross-formed yoke 12 and which thus conducts magnetization flux as well as measurement flux. FIG. 2b shows the attachment of a transducer according to the invention on a curved surface 13.

The transducers shown in FIGS. 1a–2b presuppose that the object 1 is of magnetic material. If the object, whose stresses are to be measured, is a body of non-magnetic material, for example stainless steel, copper or the like, as shown in FIGS. 3a and 3b the transducer must be modified so that it is applied on a separate part of the body in the form, for example, of a plate 14 of magnetic material provided with downwardly-facing support legs 15. The plate 14 is then attached, for example, by welding the legs 15 to the object 16 whose mechanical stress is to be measured. Thus, when the plate 14 is secured to the body, it in effect forms a part thereof so that the body has a portion of magnetic material. Such a measure may be favorable in certain cases even if the object 16 is of magnetic material, namely if magnetic conditions prevail in the object which may disturb the measuring process. To prevent a disturbing magnetic field from spreading to the measuring body, a spacer 18 of non-magnetic material may be inserted between the measuring body 14 and the object 16. The desirable magnetic isolation can also be achieved by substituting for the bent leg 15, welded-on pieces of non-magnetic material such as austenitic steel, serving as both legs and magnetic isolation. The body 14 is connected to the object 16 so rigidly that it will follow proportionally the deformation of the object, and measurement of the deformation condition of the non-magnetic material may then be performed on the body.

The embodiment according to FIGS. 3a and 3b has the advantage that the transducer may be constructed as a finished unit which may be welded to the object. The body 14 may be provided with a central hole 17 which forces the feeding flux out in the direction of measurement, which reduces the feeding effect.

We claim:

1. In combination with a body having at least a part thereof of magnetic material, means for measuring mechanical stresses in the body, comprising four pins each having one end welded to the body and one end free, the pins being located at the corners of a substantially square surface area of the body, a first winding on at least one of the pins for generating a magnetic field in the body and a second winding on at least one pin adjacent to said first pin for sensing the changes in the field configuration which occur in the body when it is subjected to mechanical forces, yokes of magnetic material each connecting the free ends of each pair of diagonally placed pins to each other, said yokes being fastened to said free ends of the pins.

2. Arrangement according to claim 1, in which the body is formed of magnetic material and said pins are welded directly thereto.

3. Arrangement according to claim 1, in which the body consists of an object of non-magnetic material having a plate of magnetic material welded thereto, said plate constituting said part of the body.

4. Arrangement according to claim 1 in which, when measuring mechanical stresses in an object of magnetic material, said four pins are welded to a plate of magnetic material constituting said part of the body, a spacer of non-magnetic material being fixed to said object, and said plate being fixed to said spacer.

* * * * *